United States Patent [19]
Muhr et al.

[11] Patent Number: 5,481,019
[45] Date of Patent: Jan. 2, 1996

[54] PROCESS FOR THE PREPARATION OF ALKALI METAL SALTS OF CYANOACETONE

[75] Inventors: Jürgen Muhr, Alfter; Marcel Feld, Köln, both of Germany

[73] Assignee: Huels Aktiengesellschaft, Marl, Germany

[21] Appl. No.: 224,151

[22] Filed: Apr. 7, 1994

[30] Foreign Application Priority Data

May 5, 1993 [DE] Germany ............ 43 14 848.4

[51] Int. Cl.$^6$ ............................ C07C 253/30
[52] U.S. Cl. ............................................ 558/451
[58] Field of Search ............................ 558/451

[56] References Cited

FOREIGN PATENT DOCUMENTS 3514688  6/1986  Germany .

OTHER PUBLICATIONS

Houben–Weyl, "Methoden der Organischen Chemie"; vol. 8 (1952) p. 573 (only p. 573 supplied).

Naturwissenschaften, vol. 33 (1946), pp. 157 and 158.

Comptes Rendus Hebdomadaires Des Seance de L'Academie des Sciences, vol. 259, No. 6 (1964), pp. 1418, 1419, 1420, Gault, et al.

*Primary Examiner*—Joseph Paul Brust
*Attorney, Agent, or Firm*—Felfe & Lynch

[57] ABSTRACT

Alkali metal salts of cyanoacetone are prepared by reacting an acetonitrile, an acetic acid ester and an alkali metal alkoxide without distilling off the alcohol formed during the reaction. The reaction products are obtained with high yields and high purity.

15 Claims, No Drawings

PROCESS FOR THE PREPARATION OF ALKALI METAL SALTS OF CYANOACETONE

FIELD OF THE INVENTION

This invention relates to a novel process for the preparation of alkali metal salts of cyanoacetone from acetonitrile, an acetic acid ester and an alkali metal alkoxide.

Alkali metal cyanoacetones having the enolic structure of the formula

$$H_3C\text{—}C(OM)\text{=}CH(CN) \qquad (I)$$

wherein M is sodium, potassium or lithium, are useful as synthetic building blocks for the preparation of pharmacologically active substances.

Background of the Invention

It is known that β-ketonitriles can be prepared by condensation of a nitrile with an aliphatic or araliphatic carboxylic acid ester (see Houben-Weyl, Vol. 8, pp. 573–574 (1952)). Aliphatic nitriles require the use of sodium amide as the condensation agent and the removal of the alcohol formed by the reaction by distillation. German Offenlegungsschrift No. 35 14 688 discloses that sodium methoxide can also be used as the condensation agent instead of sodium amide or sodium hydride, provided a larger excess of the nitrile is used and the alcohol formed by the reaction is continuously removed so as to shift the equilibrium. However, this method requires the use of carboxylic acid esters with relatively high boiling points. Methyl and ethyl acetates have too low a boiling point and distill off, as Comparative Example A below shows. On the other hand, as illustrated in Comparative Example B, acetic acid esters of longer-chain alcohols cannot be successfully used, since they are transesterified.

OBJECT OF THE INVENTION

It is an object of the present invention to provide a process for the preparation of alkali metal cyanoacetones which is simple to perform and which avoids the above mentioned disadvantages.

Other objects and advantages of the present invention will become apparent as the description thereof proceeds.

DESCRIPTION OF THE INVENTION

The above object is achieved in accordance with the present invention by a process for the preparation of alkali metal salts of cyanoacetone which comprises reacting acetonitrile with an acetic acid ester in the presence of an alkali metal alkoxide at elevated temperatures, but without distilling off the alcohol formed by the reaction. The process yields a compound of the formula I above, especially sodium cyanoacetone or potassium cyanoacetone.

Suitable acetic acid ester reactants for the process according to the present invention are those containing alkanol components in which the alkyl moiety is a substituted or unsubstituted, straight-chain, branched-chain or cyclic aliphatic radical having from 1 to 20, preferably from 1 to 6 carbon atoms. The alkyl moiety of the alcohol component may be substituted by alkyl, alkoxy, (poly)alkoxy, halogen and/or aryl radicals. Methyl acetate or ethyl acetate are preferred. Other preferable acetic acid esters are those with 3 or more carbon atoms in the alcohol moiety, if used together with alcoholates of these alcohols, which are easier to separate from acetonitrile during the work-up by distillation. Suitable alkali metal alcoholates are those in which the alcohol moiety is a substituted or unsubstituted, straight-chain, branched-chain or cyclic aliphatic radical of 1 to 20 carbon atoms. Preferred alkali metal alcoholates are those in which the alcohol moiety is that of an aliphatic alcohol of 1 to 6 carbon atoms.

Acetonitrile is preferably used in a ratio of 1 to 12 mol per mol of alkali metal alcoholate, especially from 1.5 to 6 mols of acetonitrile per mol of alkali metal alcoholate. Particular preference is given to using alkali metal alcoholates free of alcohols as the solvent. Further preference is given to the use of alkali metal alcoholates suspended in acetonitrile.

Other inert solvents may also be used, but their use is preferably avoided. Solvents such as ethers, polyethylene glycols, polyethylene glycol ethers, N-methylpyrrolidone, propylene carbonate or ethyleneurea may have positive effects upon the rheological properties and filterability, especially if they are used in amounts of 10 to 30%. Even when alcohols are not used as solvents for the alkali metal alcoholates, it is surprisingly not necessary to add other solvents.

When selecting the starting materials, it is not absolutely essential but merely preferred that the alkoxy radical in the acetic acid ester and in the alkali metal alkoxide be the same. Thus, for example, sodium cyanoacetone can be prepared from acetonitrile, ethyl acetate or methyl acetate, and sodium methoxide. Mixtures of alkali metal alkoxide and mixtures of acetic acid esters may also be used. The starting materials may be heated and caused to react in admixture with each other.

The acetic acid ester may also be added to or slowly metered into the acetonitrile and the alkali metal alkoxide, preferably a suspension thereof, at the reaction temperature. Periods of time of up to 10 hours, preferably up to 2 hours, are advantageous for this purpose. The acetic acid ester and/or a suspension of the alkali metal alkoxide and acetonitrile and/or acetonitrile and the acetic acid ester may also be added in portions or continuously under the reaction conditions.

In order to suppress the polymerization of acetonitrile in the presence of the alkali metal alkoxide during the heating phase, it is advantageous to shorten this phase by suspending the alkali metal alkoxide in some of the acetonitrile, and adding the suspension to the rest of the acetonitrile at the reaction temperature before starting to meter in the acetic acid ester. The condensation reaction is preferably performed in an inert atmosphere, such as gaseous nitrogen, at a temperature of 40° to 160° C., preferably at 80° to 120° C., under its natural pressure or at an elevated pressure of 2 to 200 bar, preferably 2 to 20 bar.

Since the removal of the alcohol by distillation is dispensed with in accordance with the present invention, the process can also be carried out in a stirring vessel or in a circulation reactor or in a cascade of stirring vessels. Surprisingly, there is little loss through self-condensation of acetonitrile or acetic acid ester, although self-condensation occurs in Comparative Examples A and B below. The work-up can be effected by filtration at 40° to 60° C., for example; in general, no dilution with acetonitrile or an alcohol is necessary for this procedure. The alkali metal salt can be converted into cyanoacetone with an acid or carbon dioxide, for example.

The following examples illustrate the present invention and will enable others skilled in the art to understand it more completely. It should be understood, however, that the invention is not limited solely to the particular examples given below.

EXAMPLE 1

500.2 g (12.2 mols) of acetonitrile and 135 g (2.5 mols). of sodium methoxide were charged into a 1.5-liter autoclave in an atmosphere of nitrogen, and the resulting suspension was heated to 90° C. while stirring. After the pressure in the autoclave was adjusted to 3 atm with gaseous nitrogen, 185 g (2.5 mols) of methyl acetate were metered into the autoclave over a period of 4 hours by means of a pressure pump. The reaction mixture was allowed to react for 30 minutes more, was then cooled to 50° C. and filtered through a pressure filter. The filter cake was washed with ethyl acetate or with acetonitrile, and dried in vacuo, yielding 183 g (more than 70% of theory) of more than 98% pure (according to HLPC) sodium cyanoacetone.

EXAMPLE 2

287 g (7 mols) of acetonitrile were charged into a 1.5-liter autoclave in an atmosphere of nitrogen, the mixture was heated to 90° C. while stirring, and then a suspension of 135 g (2.5 mols) of sodium methoxide in 213.2 g (5 mols) of acetonitrile was added. After the pressure in the autoclave was adjusted to 3 atm with gaseous nitrogen, 185 g (2.5 mols) of methyl acetate were metered into the autoclave over a period of 4 hours with the aid of a pressure pump. The reaction mixture was allowed to react for 30 minutes more, was then cooled to 50° C., filtered through a pressure filter, and the filter cake was dried, yielding 190 g (more than 71% of theory) of more than 98% pure sodium cyanoacetone.

EXAMPLE 3

492.6 g (12 mols) of acetonitrile and 204 g (3 mols) of sodium ethoxide were charged into a 1.5-liter autoclave in an atmosphere of nitrogen, and the resulting suspension was heated to 90° C. while stirring. After the pressure in the autoclave was adjusted to 3 atm with gaseous nitrogen, 352.4 g (4 mols) of ethyl acetate were metered into the autoclave over a period of 4 hours with the aid of a pressure pump. The reaction mixture was allowed to react for 30 minutes more, was then cooled to 50° C., filtered through a pressure filter, and the filter cake was dried, yielding 74% of theory of more than 97% pure sodium cyanoacetone.

EXAMPLE 4

492.6 g (12 mols) of acetonitrile and 162 g (3 mols) of sodium methoxide were charged into a 1.5-liter autoclave, the resulting suspension was heated to 90° C., and 352.4 g (4 mols) of ethyl acetate were metered into the autoclave over a period of 4 hours. The reaction mixture was allowed to react for 30 minutes more, and then the autoclave was discharged at 50° C. and the mixture was worked up as described in the preceding Examples, yielding 234 g (more than 71% of theory) of more than 95% pure sodium cyanoacetone.

EXAMPLE 5

986 g (24 mols) of acetonitrile, 108 g (2 mols) of sodium methoxide and 264 g (3 mols) of ethyl acetate were introduced into a 2-liter autoclave, and the mixture was heated to 90° C. over a period of 2 hours. Thereafter, the autoclave contents were cooled to 50° C., and the autoclave was emptied and the solids were filtered off and dried in vacuo, yielding 197.5 g (more than 83% of theory) of more than 88% pure sodium cyanoacetone.

COMPARATIVE EXAMPLE A 74.1 g (1 mol) of methyl acetate and 550 g (13.4 mols) of acetonitrile were combined in a vessel equipped with a stirrer, a dropping funnel, a gas inlet tube and a distillation column, and the mixture was heated to the boiling point while stirring and introducing nitrogen into the vessel. 180 g of a 30% by weight solution of sodium methoxide in methanol (1 mol) were added dropwise to the boiling mixture over a period of 2 hours. At the same time the low boiling point components of the reaction solution, that is, the methanol formed by the reaction and that contained in the sodium methoxide solution, the methyl acetate and the acetonitrile, were distilled off by way of the distillation column. After all of the sodium methoxide solution had been added, the distillation was continued for 3 hours more, whereby a total of 269.8 g of distillate, containing 61 g (0.82 mol) of methyl acetate were obtained. The reaction mixture was then cooled, and the precipitate formed thereby was filtered off and washed with acetone, yielding 81.5 g (15.5% of theory) of 20% pure sodium cyanoacetone.

COMPARATIVE EXAMPLE B 116.1 g (1 mol) of n-butyl acetate and 550 g (13.4 mols) of acetonitrile were combined in a vessel equipped with a stirrer, a dropping funnel, a gas inlet tube and a distillation column, and the mixture was heated to the boiling point while stirring and introducing nitrogen gas into the vessel. 180 g of a 30% solution of sodium methoxide in methanol (1 mol) were added dropwise to the boiling reaction mixture over a period of 2 hours. At the same time the methanol which vaporized out of the sodium methoxide solution, the n-butanol released by the reaction, transesterified methyl acetate and acetonitrile were distilled off. After all of the sodium methoxide solution had been added, the distillation was continued for 3 more hours, whereby a total of 531 g of distillate containing 47.8 g (0.64 mol) of methyl acetate were obtained. Thereafter, the reaction mixture was cooled, the precipitate formed thereby was filtered off and washed with acetone, yielding 32.8 g (26% of theory)of 84% pure sodium cyanoacetone.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing an alkali metal salt of cyanoacetone which comprises reacting acetonitrile with an acetic acid ester containing alkanol components in which the alkyl moiety is a substituted or unsubstituted, straight-chain, branched-chain or cyclic aliphatic radical of 1 to 20 carbon atoms, in the presence of an alkali metal alcoholate in which the alcohol moiety is a substituted or unsubstituted, straight-chain, branched-chain or cyclic aliphatic radical of 1 to 20 carbon atoms at elevated temperatures, without removing the alcohol formed by the reaction.

2. The method of claim 1, wherein said acetic acid ester is methyl acetate or ethyl acetate.

3. The method of claim 2, wherein the alcohol component of said acetic acid ester comprises 1 to 6 carbon atoms.

4. The method of claim 1, wherein said alkali metal alcoholate is sodium methoxide, sodium ethoxide or a mixture thereof.

5. The method of claim 1, wherein from 1 to 12 mols of acetonitrile are reacted per mol of alkali metal alcoholate.

6. The method of claim 1, wherein 1.5 to 6 mols of acetonitrile are reacted per mol of alkali metal alcoholate.

7. The method of claim 1, wherein from 1 to 2 mols of acetic acid ester are reacted per mol of alkali metal alcoholate.

8. The method of claim 1, wherein from 1.5 to 1.7 mols of acetic acid ester are reacted per mol of alkali metal alcoholate.

9. The method of claim 1, wherein the alcohol moiety of said alkali metal alcoholate and the alcohol moiety of said acetic acid ester are identical.

10. The method of claim 1, wherein the reaction is carried out at a temperature of 40° to 160° C. at normal pressure or at an elevated pressure of 2 to 200 bar.

11. The method of claim 1, wherein the reaction is performed at an elevated temperature of 80° to 120° C. under normal pressure or an elevated pressure of 2 to 200 bar.

12. The method of claim 1, wherein the reaction is initiated with a mixture of acetonitrile and said acetic acid ester.

13. The method of claim 1, wherein the reaction is performed by adding said acetic acid ester to a suspension of said alkali metal alkoxide in acetonitrile under the reaction conditions over a period of up to 10 hours.

14. The method of claim 1, wherein said acetic acid ester, a suspension of said alkali metal alcoholate in acetonitrile or a mixture of acetonitrile and said acetic acid ester are introduced into the reaction mixture individually or in combination with each other under the reaction conditions in portions or continuously.

15. The method of claim 1, wherein the reaction is performed with a mixture of acetic acid esters containing alkanol components in which the alcohol moiety is a substituted or unsubstituted, straight-chain, branched-chain or cyclic aliphatic radical having from 1 to 20 carbon atoms and a plurality of alkali metal alcoholates, the alcohol moieties of which are not identical.

* * * * *